United States Patent
Kawakami et al.

(10) Patent No.: US 6,838,271 B1
(45) Date of Patent: Jan. 4, 2005

(54) LOW TEMPERATURE EXPRESSION CHITINASE CDNAS AND METHOD FOR ISOLATING THE SAME

(75) Inventors: Akira Kawakami, Hokkaido (JP); Fumihiro Terami, Hokkaido (JP)

(73) Assignee: National Agricultural Research Organization (NARO), Tsukuba (JP)

( * ) Notice: Subject to any disclaimer, the term of this patent is extended or adjusted under 35 U.S.C. 154(b) by 0 days.

(21) Appl. No.: 09/534,229

(22) Filed: Mar. 24, 2000

(30) Foreign Application Priority Data

Mar. 25, 1999 (JP) .......................................... 11-081694

(51) Int. Cl.⁷ .......................... C12P 21/06; C12N 9/00; C12N 1/20; C12N 9/42; C07H 21/04
(52) U.S. Cl. ............................. 435/209; 435/4; 435/6; 435/69.1; 435/183; 435/200; 435/205; 435/206; 435/207; 435/208; 435/252.3; 435/320.1; 435/410; 435/419; 536/23.2; 536/23.6
(58) Field of Search ................................ 435/4, 6, 69.1, 435/183, 200, 205, 206, 207, 208, 252.3, 320.1, 410, 419, 195, 201; 536/23.2, 23.6

(56) References Cited

FOREIGN PATENT DOCUMENTS

WO    WO 99/06565 A2 * 2/1999

OTHER PUBLICATIONS

Bryngelsson et al. GenBank Accession X78671, Nov. 1, 1994.*

Bryngelsson et al. GenBank Accession S48847, Dec. 10, 1994.*

Liao et al. GenBank Accession, S38670, Feb. 20, 1995.*

Liao et al. GenBank Accession, X76041, Aug. 2, 1996.*

Liao et al., BioSci. Biotechnol. Biochem., vol. 103:177–187, 1994.*

* cited by examiner

*Primary Examiner*—Manjunath N. Rao
(74) *Attorney, Agent, or Firm*—Arent Fox, PLLC

(57) ABSTRACT

A winter wheat-derived chitinase cDNA is provided which has a nucleotide sequence corresponding to an amino acid sequence listed as SEQ. ID. No.1 in FIG. 1. Another winter wheat-derived chitinase cDNA is provided which has a nucleotide sequence corresponding to an amino acid sequence listed as SEQ. ID. No.2 in FIG. 2. Further, a winter wheat-derived chitinase cDNA is provided which has a nucleotide sequence corresponding to an amino acid sequence listed as SEQ. ID. No.3 in FIG. 3. Moreover, a method is provided for isolating the above three kinds of chitinase cDNAs.

10 Claims, 2 Drawing Sheets

FIG.1

AMINO ACID SEQUENCE OF SEQ. ID No1.

```
         10         20         30         40         50         60
MARFAALAVC AAALLLAVAA GGAAAQGVGS VITRSVYASM LPNRDNSLCP ARGFYTYDAF 70         80         90        100        110        120
IAAANTFPGF GTTGSADDIK RDLAAFFGQT SHETTGGTRG AADQFQWGYC FKEEISKATS 130        140        150        160        170        180
PPYYGRGPIQ LTGRSNYDLA GRAIGKDLVS NPDLVSTDAV VSFRTAMWFW MTAQGNKPSC 190        200        210        220        230        240
HNVALRRWTP TAADTAAGRV PGYGVITNII NGGLECGMGR NDANVDRIGY YTRYCGMLGT 250        260        270        280        290        300
ATGGNLDCYT QRNFAS*... .......... .......... .......... ..........
```

FIG.2

AMINO ACID SEQUENCE OF SEQ. ID No2.

```
         10         20         30         40         50         60
MSTLRARCAT AVLAVVLAAA AVTPATAEQC GSQAGGAKCA DCLCCSQFGF CGTTSDYCGP 70         80         90        100        110        120
RCQSQCTGCG GGGGGVASIV SRDLFERFLL HRNDAACLAR GFYTYDAFLA AAGAFPAFGT 130        140        150        160        170        180
TGDLDTRKRE VAAFFGQTSH ETTGGWPTAP DGPFSWGYCF KQEQGSPPSY CDQSADWPCA 190        200        210        220        230        240
PGKQYYGRGP IQLTHNYNYG PAGRAIGVDL LNNPDLVATD PTVAFKTAIW FWMTTQSNKP 250        260        270        280        290        300
SCHDVITGLW TPTARDSAAG RVPGYGVITN VINGGIECGM GQNDKVADRI GFYKRYCDIF 310        320        330        340        350        360
GIGYGNNLDC YNQLSFNVGL AAQ*...... .......... .......... ..........
```

FIG.3

AMINO ACID SEQUENCE OF SEQ. ID No3.

```
         10         20         30         40         50         60
MRGVVVVAML AAAFAVSAHA EQCGSQAGGA TCPNCLCCSK FGFCGTTSDY CGTGCQSQCN 70         80         90        100        110        120
GCSGGTPVPV PTPSGGGVSS IISQSLFDQM LLHRNDAACL AKGFYNYGAF VAAANSFSGF 130        140        150        160        170        180
ATTGSTDVKK REVAAFLAQT SHETTGGWPT APDGPYSWGY CFNQERGATS DYCTPSSQWP 190        200        210        220        230        240
CAPGKKYFGR GPIQISHNYN YGPAGQAICT DLLNNPDLVA SDATVSFKTA LWFWMTPQSP 250        260        270        280        290        300
KPSSHDVITG RWSPSGADQA AGRVPGYGVI TNIINGGLEC GRGQDGRVAD RIGFYKRYCD 310        320        330        340        350        360
LLGVSYGDNL DCYNQRPFA* .......... .......... .......... ..........
```

LOW TEMPERATURE EXPRESSION CHITINASE CDNAS AND METHOD FOR ISOLATING THE SAME

BACKGROUND OF THE INVENTION

The present invention relates to chitinase cDNAs and to a method for their isolation, and more specifically it relates to chitinase cDNAs having a function of conferring plant disease resistance under low temperature, and to a method of isolating the chitinase cDNAs.

In the northern regions, overwintering crops such as barley, forage grasses and wheat must survive subzero temperature (0° C. or below 0° C.) and a long-lasting snow cover condition (0° C. in darkness). However, overwintering crops in such environment are often attacked by snow molds which are a diverse group of psychrophilic parasitic fungi. This biotic stress greatly limits yields and quality of biennial or perennial crops, in the same manner as a low temperature stress will do in the northern region with snow accumulation.

In current winter wheat cultivation, it is necessary to apply a broad-spectrum fungicides before a continuous snow cover for protecting the plant from snow molds infection.

However, it has taken high cost and it has been proved difficult to apply the fungicide at the effective time, because of unstable nature of the start of a snow cover every year.

In view of the above, it has been desired to raise a plant variety having a high disease resistance under tow temperature environment.

Nevertheless, up till now, when using several conventional breeding methods each based on cross-breeding, it has not been possible to raise superior varieties with high resistance, and a long time (many years) is required for raising superior varieties. For this reason, there has been a strong demand for variety improvement by more effective methods such as gene engineering methods.

As a result of repeated diligent research over years aimed at solving the problems described above, the inventors of the present invention have arrived at the following conclusion. Specifically, it has been found that plant disease resistance under low temperature environment is induced by cold acclimation that occurs under a low temperature from autumn through winter (hereunder referred to as "hardening") and that expression of the three chitinase cDNAs of the invention described hereunder are found during this hardening, with the translation product conferring plant disease resistance through digestion of chitin, one of the major components of fungus cell wall.

SUMMARY OF THE INVENTION

It is therefore an object of the present invention to provide chitinase cDNAs that encode proteins having enzymatic function in low temperature environments and that when introduced into plants confer plant disease resistance.

It is another object of the invention to provide a method for isolation of chitinase cDNAs that encode Proteins having enzymatic function in low temperature environments and that when introduced into plants confer plant disease resistance.

According to one aspect of the present invention, there is provided a winter wheat-derived chitinase cDNA, characterized in that said cDNA has a nucleotide sequence corresponding to an amino acid sequence listed as SEQ. ID. No.1 in FIG. 1. In detail, said cDNA comprises 771 nuclcotides/ 256 amino acids and has 98% identity (on amino acid sequence level) with barley-derived chitinase cDNA. In more detail, said cDNA encodes a protein with chitinase activity in low temperature environment and confers plant disease resistance by digestion of chitin, one of the major components of fungus cell wall.

According to another aspect of the present invention, there is provided another winter wheat-derived chitinase cDNA, characterized in that said cDNA has a nucleotide sequence corresponding to an amino acid sequence listed as SEQ. ID. No.2 in FIG. 2. In detail, said cDNA comprises 972 nucleotides/323 amino acids and has 68% identity (on amino acid sequence level) with rye-derived chitinase cDNA. In more detail, said cDNA encodes a protein with chitinase activity in low temperature environment and confers plant disease resistance by digestion of chitin, one of the major components of fungus cell wall.

According to a further aspect of the present invention, there is provided a further winter wheat-derived chitinase cDNA, characterized in that said cDNA has a nucleotide sequence corresponding to an amino acid sequence listed as SEQ. ID. No.3 in FIG. 3. In detail, said cDNA comprises 960 nucleotides/319 amino acids and has 95% identity (on amino acid sequence level) with spring wheat-derived chitinase cDNA. In more detail, said cDNA encodes a protein with chitinase activity in low temperature environment and confers plant disease resistance by digestion of chitin, one of the major components of fungus cell wall.

According to a still further aspect of the present invention, there is provided a method of isolating a winter wheat-derived chitinase cDNA having a nucleotide sequence corresponding to an amino acid sequence listed as SEQ. ID. No.1 in FIG. 1, a winter wheat-derived chitinase cDNA having a nucleotide sequence corresponding to an amino acid sequence listed as SEQ. ID. No.2 in FIG. 2, a winter wheat-derived chitinase cDNA having a nucleotide sequence corresponding to an amino acid sequence listed as SEQ. ID. No.3 in FIG. 3, said method comprising the steps of: extracting mRNA from winter wheat variety PI173438 (having high snow molds resistance) that has undergone a sufficient hardening Process; preparing cDNA and a cDNA library based on said mRNA; analyzing nucleotide sequences of a number of Plant-derived chitinase cDNAs which have all been published by EMBL/Genebank/ DDBJDNA Databank; designing an air of chitinase cDNA-specific degenerated primers with reference to highly conserved nucleotide sequence portions of the plant-derived chitinase cDNAs; conducting PCR (polymerase chain reaction) using a pair of chitinase cDNA-specific degenerated primers and using said cDNA as a template, thereby amplifying fragments of chitinase cDNAs and obtaining amplified DNA fragments; and using said to amplified DNA fragments as probes for screening said cDNA library by a hybridization assay, to isolate recombinant plaques containing full length of cDNA.

In particular, one of the pair of chitinase cDNA-specific degenerated primers has the following nucleotide sequence:

(Forward): 5' C-A-C-G-A-G-A-C-C-A-C-N-G-G-C-G-G-N-T-C-C-G-C (SEQ. ID. No.4), and the other has the following nucleotide sequence:

(Reverse)d: 5' A-C-N-A-A-T-A-T-C-A-T-C-A-A-C-G-G-C-G-G (SEQ. ID. No.5).

BRIEF DESCRIPTION OF THE DRAWINGS

FIG. 1 shows an amino acid sequence of SEQ. ID No.1.

FIG. 2 shows an amino acid sequence of SEQ. ID No.2.

FIG. 3 shows an amino acid sequence of SEQ. ID No.3.

DETAILED DESCRIPTION OF THE PREFERRED EMBODIMENTS

The cDNAs of the present invention are chitinase cDNAs capable of expressing under a low temperature condition.

The method for isolating the cDNAs of the present invention may be carried out in the following manner.

Specifically, mRNA is extracted from winter wheat PI1173438 (having high snow molds resistance) that has undergone a hardening process (low temperature acclimation) under natural conditions in Sapporo City, Japan until November 22. This mRNA is then used to prepare cDNA and a cDNA library.

Next, nucleotide sequences of a number of plant-derived chitinase cDNAs which have all been published by EMBL/Genebank/DDBJDNA Databank are closely analyzed, and a pair of chitinase cDNA-specific degenerated primers are designed with reference to highly conserved nucleotide sequence portions.

The pair of designed chitinase cDNA-specific degenerated primers are used in a PCR (polymerase chain reaction) using the above-mentioned cDNA as the template for amplifying the expected chitinase cDNA fragments (all are approximately 400 bp), and the amplified fragments are isolated.

The amplified fragments are used as probes for screening the cDNA library by a hybridization assay, to isolate recombinant plaques containing full length of cDNA. The nucleotide sequences of the isolated plaques were analyzed and demonstrated to be three different chitinase cDNAs which are three kinds of chitinase cDNA fragments, all are novel in plants.

An example of the method for isolating the cDNAs of the present invention was carried out in the following steps 1)–2)

1) Preparation of cDNA and cDNA Library from Snow Molds Resistant Winter Wheat Variety PI173438 mRNA was extracted by a common method from the crown portion of winter wheat (*Triticum astivum L.*) PI173438 (having high snow molds resistance) that had been seeded in a container in late September and had then undergone a hardening process under natural conditions until November 22. A portion (5 µg) of the obtained mRNA was used to synthesize cDNA utilizing a cDNA Synthesis Kit (STRATAGENE Co.) After attaching adaptors to both ends of the cDNA, it was incorporated into a ZAP Expression Vector (STRATAGENE Co.) thereby obtaining a cDNA library of approximately 6×10⁶ pfu.

2) PCR using a Pair of cDNA-specific Degenerated Primers and using the cDNA as a Template One of the pair of chitinase cDNA-specific degenerated primers, having the following nucleotide sequence: (Forward): 5' C-A-C-G-A-G-A-C-C-A-C-N-G-G-C-G-G-N-T-G-G-C (SEQ. ID. No.4), the other chitinase cDNA-specific degenerated primer, having the following nucleotide sequence: (Reverse): 5' A-C-N-A-A-T-A-T-C-A-T-C-A-A-C-G-G-C-G-G (SEQ. ID. No.5).

which were synthesized based on highly conserved regions of the nucleotide sequences of known chitinase cDNAs (published by EMBL/Genebank/DDBJDNA Databank), were used in a PCR using the cDNA (synthesized in the manner described in the above) as the template.

The PCR was performed in a final volume of 50 µl. In detail, 1 µl of Taq DNA polymerase (5 units/µl by Nippon Gene Co., 5 µl of 10×PCR buffer (containing MgCl₂), 5 µl of dNTP solution (10 mM), 2 µl of each primer (12 µM) and about 10 ng of the cDNA synthesized in the above, were mixed and then brought to a total of 50 µl with distilled water. The PCR conditions and number of reaction cycles are shown in Table 1 below.

TABLE 1

| PCR condition and number of reaction cycles | | | |
|---|---|---|---|
| Initial Denaturation | 94° C. | 1 min | once |
| Denaturation | 94° C. | 1 min | |
| Annealing | 48° C. | 1 min | |
| Primer Extension | 72° C. | 1 min | 30 cycles |
| Final Extension | 72° C. | 2 min | once |

(In Table 1, "denaturation" refers to a reaction in which double-stranded DNA is melt into single strand and secondary structure is eliminated, "primer extension" refers to an synthesizing of the new complementary strand, and "30 cycles" means that three basic steps of denaturation-annealing-primer extension are repeated with 30 cycles.

As a result, DNA fragments (having expected length of approximately 400 bp) of chitinase cDNAs were amplified by the above PCR with the pair of chitinase cDNA-specific degenerated primer having nucleotide sequence of SEQ. ID No.4 and the primer with the nucleotide sequence of SEQ. ID No.5. Theses amplified DNA fragments were then isolated and subsequently sequenced using a DNA sequencer (Model 373S by ABI Co.) according to the conventional method. By comparing the sequences with known chitinase, it were confirmed that novel chitinase cDNA fragments (having a high homology with known chitinase cDNA) were isolated.

3) Isolation and Nucleotide Sequencing of Full Length cDNAs Encoding Chitinase of the Present Invention About 1×10⁵ recombinant plaques from the cDNA library obtained in the manner described in the above were subjected to a hybridization assay by using filters lifted with 1×10⁵ recombinant plaques, and using probes prepared by labeling (with $^{32}p$) each novel chitinase cDNA fragment obtained in the above.

The hybridization reaction was carried out for 16 hours at 42° C., in a solution containing 50% formamide, 5×SSPE, 5×Denhardt's solution, 0.5% SDS and 0.2 mg/ml salmon sperm DNA with $^{32}$P-labeled probe.

The fillers were then washed twice in a solution containing 2×SSC and 0.1% SDS at 65° C. for 10 min. Afterwards, the filters were washed twice with another washing solution containing 0.1×SSC and 0.1% SDS, at 65° C. for 15 min. Detection of each positive plaque binding to $^{32}$P-labed probe was performed by exposing above washed filters to X-ray films.

About 45 positive recombinant plaques obtained in the above were subjected to nucleotide sequencing with DNA sequencer by ABI Co.

Analysis of the nucleotide sequences of these recombinant plaques revealed that novel chitinase cDNAs having nucleotide sequences corresponding to the amino acid sequences listed as SEQ. ID Nos. 1–3 in FIGS. 1–3 had been isolated from winter wheat variety PI173438.

In fact, what were isolated were i) a novel winter wheat-derived chitinase cDNA having a nucleotide sequence corresponding to the amino acid sequence listed as SEQ. ID. No.1 in FIG. 1, comprising 771 nucleotides/256 amino acids and having 98% identity (on amino acid sequence level) with barley-derived chitinase cDNA, ii) a novel winter wheat-derived chitinase cDNA having a nucleotide sequence corresponding to the amino acid sequence listed as SEQ. ID. No.2 in FIG. 2, comprising 972 nucleotides/323 amino acids and having 68% identity (on amino acid sequence level) with rye-derived chitinase cDNA, iii) a novel winter wheat-derived chitinase cDNA having a nucleotide sequence corresponding to the amino acid sequence listed as SEQ. ID. No. 3 in FIG. 3, comprising 960 nucleotides/319 amino acids and having 95% identity (on amino acid sequence level) with spring wheat-derived chitinase cDNA.

Investigation of Enzymatic Activity

In order to investigate enzymatic activities of the novel chitinase cDNAs of the present invention, enzymatic reactions were conducted under the following conditions using culture solutions containing novel proteins secreted by recombinant yeast (into which each novel chitinase cDNA of the present invention has been introduced).

[Enzymatic Reaction Condition]

Buffer solution (20 mM citric acid/phosphoric acid). pH 4.5

Final substrate concentration: 1% collidal chitin

Reaction temperature: 38° C. reaction time: 16 hours.

As a result, it was confirmed that the culture solutions containing novel proteins secreted by recombinant yeast (into which each novel chitinase cDNA of the present invention has been introduced) had a chitinase activity capable of producing a disaccharide (a chito-oligosaccharide) or a trisaccharide (another chito-oligosaccharide) from chitin polymer (serving as a substrate).

The nucleotide sequences of the novel cDNAs obtained in the present invention are listed in the following.

Nucleotide Sequence of cDNA Corresponding to
the Acid Sequence Listed as SEQ. ID. No.1 (SEQ.
ID. No:6)

```
          10         20         30         40         50         60
ATGGCGAGGT TTGCTGCCCT CGCCGTGTGC GCCGCCGCGC TCCTGCTCGC CGTGGCGGCG 70         80         90        100        110        120
GGGGGTGCCG CGGCGCAGGG CGTGGGCTCG GTCATCACGC GGTCGGTGTA CGCGAGCATG 130        140        150        160        170        180
CTGCCCAACC GCGACAACTC GCTGTGCCCG GCCACAGGGT TCTACACGTA CGACGCCTTC 190        200        210        220        230        240
ATCGCCGCCG CCAACACCTT CCCCGGGCTT CGGCACCACCG GCAGCGCCGA CGACATCAAG 250        260        270        280        290        300
CGCGACCTCG CCGCCTTCTT CGGCCAGACC TCCCACGAGA CCACCGGAGG GACGAGAGGC 310        320        330        340        350        360
GCTGCCGACC AGTTCCAGTG GGGCTACTGC TTCAAGGAAG AGATAAGCAA GGCCACGTCC 370        380        390        400        410        420
CCACCATACT ATGGACGGGG ACCCATCCAA TTGACAGGGC GGTCCAACTA CGATCTTGCC 430        440        450        460        470        480
GGGAGAGCGA TCGGGAAGGA CCTGGTGAGC AACCCAGACC TAGTGTCCAC GGACGCGGTG 490        500        510        520        530        540
GTGTCCTTCA GGACGGCCAT GTGGTTCTGG ATGACGGCGC AGGGAAACAA GCCGTCGTGC 550        560        570        580        590        600
CACAACGTCG CCCTACGCCG CTGGACGCCG ACGGCCGCCG ACACCGCTGC CGGCAGGGTA 610        620        630        640        650        660
CCCGGATACG GAGTGATCAC CAATATCATC AACGGCGGGC TCGAGTGCGG AATGGGCCGG 670        680        690        700        710        720
```

```
                                  -continued
AACGACGCCA ACGTCGACCG CATCGGCTAC TACACGCGCT ACTGCGGCAT GCTCGGCACG 730        740        750        760        770        780
GCCACCGGAG GCAACCTCGA CTGCTACACC CAGAGGAACT TCGCTAGCTA G.........
```

Nucleotide Sequence of cDNA Corresponding to
the Amino Acid Sequence Listed as SEQ. ID. No.2
(SEQ. ID. No:7)

```
         10         20         30         40         50         60
ATGTCCACGC TGAGAGCGCG GTGTGCGACG GCCGTCCTGG CCGTCGTCCT GGCGGCGGCC 70         80         90        100        110        120
GCGGTCACGC CGGCCACGGC CGAGCAGTGC GGCTCGCAAG CCGGCGGCGC CAAGTGCGCC 130        140        150        160        170        180
GACTGCCTGT GCTGCAGCCA GTTCGGGTTC TGCGGCACCA CCTCCGACTA CTGCGGCCCC 190        200        210        220        230        240
CGCTGCCAGA GCCAGTGCAC TGGCTGCGGT GGCGGCGGCG GCGGGGTGGC CTCCATCGTG 250        260        270        280        290        300
TCCAGGGACC TCTTCGAGCG GTTCCTGCTC CATCGCAACG ACGCAGCGTG CCTGGCCCGC 310        320        330        340        350        360
GGGTTCTACA CGTACGACGC CTTCTTGGCC GCCGCCGGCG CGTTCCCGGC CTTCCGCACC 370        380        390        400        410        420
ACCGGAGACC TGGACACGCG GAAGCGGGAG GTGGCGGCCT TCTTCGGCCA CACCTCTCAC 430        440        450        460        470        480
GAGACCACCG GCGGGTGGCC CACCGCGCCC GACGGCCCCT TCTCATGGGG CTACTGCTTC 490        500        510        520        530        540
AAGCAGGAGC AGGGCTCGCC GCCGAGCTAC TGCGACCAGA GCGCCGACTG GCCGTGCGCA 550        560        570        580        590        600
CCCGGCAAGC AGTACTATGG CCGCGGCCCC ATCCAGCTCA CCCACAACTA CAACTACGGA 610        620        630        640        650        660
CCGGCGGGCC GCGCAATCGG GGTGGACCTG CTGAACAATC CGGACCTGGT GGCCACGGAC 670        680        690        700        710        720
CCGACAGTGG CGTTCAAGAC GGCGATATGG TTCTGGATGA CGACGCAGTC CAACAAGCCG 730        740        750        760        770        780
TCGTGCCATG ACGTGATCAC GGGGCTGTGG ACTCCGACGG CCAGGGATAG CGCAGCCGGA 790        800        810        820        830        840
CGGGTACCCG GGTATGGTGT CATCACCAAC GTCATCAACG GCGGGATCGA ATGCGGCATG 850        860        870        880        890        900
GGGCACAACG ACAAGGTGGC GGATCGGATC GGGTTCTACA AGCGCTATTG TGACATTTTC 910        920        930        940        950        960
GGCATCGGCT ACGGGAATAA CCTCGACTGC TACAACCAAT TGTCGTTCAA CGTTGGGCTC 970        980        990       1000       1010       1020
GCGGCACAGT GA........ .......... .......... .......... ..........
```

Nucleotide Sequence of cDNA Corresponding to
the Amino Acid Sequence Listed as SEQ. ID. No.3
(SEQ. ID. No:8)

```
         10         20         30         40         50         60
ATGAGAGGAG TTGTGGTGGT GGCCATGCTG GCCGCGGCCT TCGCCGTGTC TGCGCACGCC 70         80         90        100        110        120
GAGCAATGCG GCTCGCAGGC CGGCGGGGCG ACGTGCCCCA ACTGCCTCTG CTGCAGCAAG 130        140        150        160        170        180
TTCGGTTTCT GCGGCACCAC CTCCGACTAC TGCGGCACCG GCTGCCAGAG CCAGTGCAAT
```

-continued

```
        190        200        210        220        230        240
GGCTGCAGCG GCGGCACCCC GGTACCGGTA CCGACCCCCT CCGGCGGCGG CGTCTCCTCC 250        260        270        280        290        300
ATTATCTCGC AGTCGCTCTT CGACCAGATG CTGCTGCACC GCAACGACGC GGCGTGCCTG 310        320        330        340        350        360
GCCAAGGGGT TCTACAACTA CGGCGCCTTC GTCGCCGCCG CCAACTCGTT CTCGGGCTTC 370        380        390        400        410        420
GCGACCACAG GTAGCACCGA CGTCAAGAAG CGCGAGGTGG CCGCGTTCCT CGCTCAGACT 430        440        450        460        470        480
TCCCACGAGA CGACCGGCGG GTGGCCGACG GCGCCCGACG GCCCCTACTC CTGGGGCTAC 490        500        510        520        530        540
TGCTTCAACC AGGAGCGCGG CGCCACCTCC GACTACTGCA CGCCGAGCTC GCAGTGGCCA 550        560        570        580        590        600
TGTGCGCCGG GCAAGAAGTA CTTCGGGCGC GGGCCCATCC AGATCTCACA CAACTACAAC 610        620        630        640        650        660
TACGGGCCGG CGGGGCAGGC CATCGGCACC GACCTGCTCA ACAACCCGGA CCTTGTGGCG 670        680        690        700        710        720
TCGGACGCGA CCGTGTCGTT TAAGACGGCG TTGTGGTTCT GGATGACGCC GCAATCACCC 730        740        750        760        770        780
AAGCCTTCGA GCCACGACGT GATCACGGGC CGGTGGAGCC CCTCGGGCGC CGACCAGGCG 790        800        810        820        830        840
GCGGGGAGGG TGCCTGGGTA CGGTGTGATC ACCAACATCA TCAACGGTGG GCTCGAGTGC 850        860        870        880        890        900
GGGCGCGGGC AGGACGGCCG TGTCCCCGAC CGGATCGGGT TCTACAAGCG CTACTGCGAC 910        920        930        940        950        960
CTCCTTGGCG TCAGCTACGG TGACAACCTG GACTGCTACA ACCAAAGGCC GTTCGCATAG 970        980        990       1000       1010       1020
.......... .......... .......... .......... .......... ..........
```

The advantages of the present invention may be concluded as follows.

According to the present invention there are provided novel chitinase cDNAs in wheat that have different amino acid sequences from known chitinase cDNAs and confer high disease resistance in low temperature environment. Because the three chitinase cDNAs of the present invention are capable of digesting chitin at low temperature, the introduction of any one of these three different chitinase cDNAs into plants can confer plant disease resistance in low temperature environments, so that plant varieties can be provided with high resistance against psychrophilic plant pathogens such as snow molds.

While the presently preferred embodiments of the this invention have been shown and described above, it is to be understood that these disclosures are for the purpose of illustration and that various changes and modifications may be made without departing from the scope of the invention as set forth in the appended claims.

What is claimed is:

1. An isolated winter wheat chitinase cDNA wherein said cDNA encodes a protein with chitinase activity at low temperatures of 0° C. or below, and wherein said cDNA comprises 771 nucleotides which encode an amino acid sequence comprising 250 amino acids that is 98% identical with an amino acid sequence encoded by nucleotide sequence SEQ ID No:6.

2. A winter wheat chitinase cDNA according to claim 1, wherein said cDNA has nucleotide sequence that encodes an amino acid sequence listed as SEQ ID No:1 in FIG. 1.

3. An isolated winter wheat chitinase cDNA characterized in that said cDNA encodes a protein with chitinase activity at low temperatures of 0° C. or below, and wherein said cDNA comprise 972 nucleotides which encode an amino acid sequence comprising 323 amino acids that is 68% identical with an amino acid sequence encoded by nucleotide sequence SEQ ID No: 7.

4. A winter wheat chitinase cDNA according to claim 3, wherein said cDNA has nucleotide sequence that encodes an amino acid sequence listed as SEQ ID No:2 in FIG. 2.

5. An isolated winter wheat chitinase cDNA wherein said cDNA encodes a protein with chitinase activity at low temperatures of 0° C. or below, and wherein said cDNA comprises 960 nucleotides which encode an amino acid sequence comprising 319 amino acids that is 95% identical with an amino acid sequence encoded by nucleotide sequence SEQ ID No:8.

6. A winter wheat chitinase cDNA according to claim 5, wherein said cDNA has a nucleotide sequence that encodes an amino acid sequence listed as SEQ ID No:3 in FIG. 3.

7. A method of isolating a winter wheat chitinase cDNA having a nucleotide sequence that encodes an amino acid sequence listed as SEQ ID No:1 in FIG. 1, a winter wheat chitinase cDNA having a nucleotide sequence that encodes an amino acid sequence listed as SEQ ID No:2 in FIG. 2, or a winter wheat chitinase cDNA having a nucleotide sequence that encodes to an amino acid sequence listed as SEQ ID No:3 in FIG. 3, said method comprising the steps of:

extracting mRNA from winter wheat variety that has undergone a sufficient hardening process:

preparing a cDNA library based on said mRNA;

analyzing nucleotide sequences of a number of plant-derived chitinase cDNAs which have all been published by EMBL/Genebank/DDBJDNA Databank;

designing a pair of chitinase cDNA-specific degenerated primers with reference to highly conserved nucleotide sequence portions of the plant-derived chitinase cDNAs;

conducting PCR (polymerase chain reaction) using a pair of chitinase cDNA-specific degenerated primers and using said cDNA as a template, thereby amplifying fragments of chitinase cDNAs and obtaining amplified DNA fragments; and using said amplified DNA fragments as probes for screening said cDNA library by a hybridization assay, to isolate recombinant plaques containing full length cDNA.

8. The method according to claim 7, wherein one of said pair of chitinase cDNA-specific degenerated primers has the following nucleotide sequence:

(Forward): 5' C-A-C-G-A-G-A-C-C-A-C-N-G-G-C-G-G-N-T-G-G-C (SEQ ID No:4), and the other has the following nucleotide sequence:

(Reverse): 5' A-C-N-A-A-T-A-T-C-A-T-C-A-A-C-G-G-C-G-G (SEQ ID No:5).

9. A plant transformed with a cDNA according to claim 2.

10. The winter wheat chitinase cDNA of claim 2, wherein the cDNA synthesized from mRNA extracted from winter wheat.

* * * * *

SEQUENCE LISTING

```
<160> NUMBER OF SEQ ID NOS: 8

<210> SEQ ID NO 1
<211> LENGTH: 256
<212> TYPE: PRT
<213> ORGANISM: Triticum aestivum

<400> SEQUENCE: 1

Met Ala Arg Phe Ala Ala Leu Ala Val Cys Ala Ala Ala Leu Leu Leu
1               5                   10                  15

Ala Val Ala Ala Gly Gly Ala Ala Ala Gln Gly Val Gly Ser Val Ile
            20                  25                  30
```

```
Thr Arg Ser Val Tyr Ala Ser Met Leu Pro Asn Arg Asp Asn Ser Leu
        35                  40                  45

Cys Pro Ala Arg Gly Phe Tyr Thr Tyr Asp Ala Phe Ile Ala Ala Ala
 50                  55                  60

Asn Thr Phe Pro Gly Phe Gly Thr Gly Ser Ala Asp Asp Ile Lys
65                  70                  75                  80

Arg Asp Leu Ala Ala Phe Phe Gly Gln Thr Ser His Glu Thr Thr Gly
                 85                  90                  95

Gly Thr Arg Gly Ala Ala Asp Gln Phe Gln Trp Gly Tyr Cys Phe Lys
                100                 105                 110

Glu Glu Ile Ser Lys Ala Thr Ser Pro Pro Tyr Tyr Gly Arg Gly Pro
            115                 120                 125

Ile Gln Leu Thr Gly Arg Ser Asn Tyr Asp Leu Ala Gly Arg Ala Ile
        130                 135                 140

Gly Lys Asp Leu Val Ser Asn Pro Asp Leu Val Ser Thr Asp Ala Val
145                 150                 155                 160

Val Ser Phe Arg Thr Ala Met Trp Phe Trp Met Thr Ala Gln Gly Asn
                165                 170                 175

Lys Pro Ser Cys His Asn Val Ala Leu Arg Arg Trp Thr Pro Thr Ala
            180                 185                 190

Ala Asp Thr Ala Ala Gly Arg Val Pro Gly Tyr Gly Val Ile Thr Asn
        195                 200                 205

Ile Ile Asn Gly Gly Leu Glu Cys Gly Met Gly Arg Asn Asp Ala Asn
210                 215                 220

Val Asp Arg Ile Gly Tyr Tyr Thr Arg Tyr Cys Gly Met Leu Gly Thr
225                 230                 235                 240

Ala Thr Gly Gly Asn Leu Asp Cys Tyr Thr Gln Arg Asn Phe Ala Ser
                245                 250                 255

<210> SEQ ID NO 2
<211> LENGTH: 323
<212> TYPE: PRT
<213> ORGANISM: Triticum aestivum

<400> SEQUENCE: 2

Met Ser Thr Leu Arg Ala Arg Cys Ala Thr Ala Val Leu Ala Val Val
1               5                   10                  15

Leu Ala Ala Ala Val Thr Pro Ala Thr Ala Glu Gln Cys Gly Ser
                20                  25                  30

Gln Ala Gly Gly Ala Lys Cys Ala Asp Cys Leu Cys Cys Ser Gln Phe
            35                  40                  45

Gly Phe Cys Gly Thr Thr Ser Asp Tyr Cys Gly Pro Arg Cys Gln Ser
 50                  55                  60

Gln Cys Thr Gly Cys Gly Gly Gly Gly Val Ala Ser Ile Val
65                  70                  75                  80

Ser Arg Asp Leu Phe Glu Arg Phe Leu Leu His Arg Asn Asp Ala Ala
                85                  90                  95

Cys Leu Ala Arg Gly Phe Tyr Thr Tyr Asp Ala Phe Leu Ala Ala
            100                 105                 110

Gly Ala Phe Pro Ala Phe Gly Thr Thr Gly Asp Leu Asp Thr Arg Lys
        115                 120                 125

Arg Glu Val Ala Ala Phe Phe Gly Gln Thr Ser His Glu Thr Thr Gly
        130                 135                 140

Gly Trp Pro Thr Ala Pro Asp Gly Pro Phe Ser Trp Gly Tyr Cys Phe
145                 150                 155                 160
```

-continued

Lys Gln Glu Gln Gly Ser Pro Pro Ser Tyr Cys Asp Gln Ser Ala Asp
                165                 170                 175

Trp Pro Cys Ala Pro Gly Lys Gln Tyr Tyr Gly Arg Gly Pro Ile Gln
            180                 185                 190

Leu Thr His Asn Tyr Asn Tyr Gly Pro Ala Gly Arg Ala Ile Gly Val
        195                 200                 205

Asp Leu Leu Asn Asn Pro Asp Leu Val Ala Thr Asp Pro Thr Val Ala
    210                 215                 220

Phe Lys Thr Ala Ile Trp Phe Trp Met Thr Thr Gln Ser Asn Lys Pro
225                 230                 235                 240

Ser Cys His Asp Val Ile Thr Gly Leu Trp Thr Pro Thr Ala Arg Asp
                245                 250                 255

Ser Ala Ala Gly Arg Val Pro Gly Tyr Gly Val Ile Thr Asn Val Ile
            260                 265                 270

Asn Gly Gly Ile Glu Cys Gly Met Gly Gln Asn Asp Lys Val Ala Asp
        275                 280                 285

Arg Ile Gly Phe Tyr Lys Arg Tyr Cys Asp Ile Phe Gly Ile Gly Tyr
    290                 295                 300

Gly Asn Asn Leu Asp Cys Tyr Asn Gln Leu Ser Phe Asn Val Gly Leu
305                 310                 315                 320

Ala Ala Gln

<210> SEQ ID NO 3
<211> LENGTH: 319
<212> TYPE: PRT
<213> ORGANISM: Triticum aestivum

<400> SEQUENCE: 3

Met Arg Gly Val Val Val Ala Met Leu Ala Ala Phe Ala Val
1               5                   10                  15

Ser Ala His Ala Glu Gln Cys Gly Ser Gln Ala Gly Gly Ala Thr Cys
                20                  25                  30

Pro Asn Cys Leu Cys Cys Ser Lys Phe Gly Phe Cys Gly Thr Thr Ser
            35                  40                  45

Asp Tyr Cys Gly Thr Gly Cys Gln Ser Gln Cys Asn Gly Cys Ser Gly
    50                  55                  60

Gly Thr Pro Val Pro Val Pro Thr Pro Ser Gly Gly Val Ser Ser
65                  70                  75                  80

Ile Ile Ser Gln Ser Leu Phe Asp Gln Met Leu Leu His Arg Asn Asp
                85                  90                  95

Ala Ala Cys Leu Ala Lys Gly Phe Tyr Asn Tyr Gly Ala Phe Val Ala
            100                 105                 110

Ala Ala Asn Ser Phe Ser Gly Phe Ala Thr Thr Gly Ser Thr Asp Val
    115                 120                 125

Lys Lys Arg Glu Val Ala Ala Phe Leu Ala Gln Thr Ser His Glu Thr
    130                 135                 140

Thr Gly Gly Trp Pro Thr Ala Pro Asp Gly Pro Tyr Ser Trp Gly Tyr
145                 150                 155                 160

Cys Phe Asn Gln Glu Arg Gly Ala Thr Ser Asp Tyr Cys Thr Pro Ser
                165                 170                 175

Ser Gln Trp Pro Cys Ala Pro Gly Lys Lys Tyr Phe Gly Arg Gly Pro
            180                 185                 190

Ile Gln Ile Ser His Asn Tyr Asn Tyr Gly Pro Ala Gly Gln Ala Ile
        195                 200                 205

```
Gly Thr Asp Leu Leu Asn Asn Pro Asp Leu Val Ala Ser Asp Ala Thr
         210                 215                 220

Val Ser Phe Lys Thr Ala Leu Trp Phe Trp Met Thr Pro Gln Ser Pro
225                 230                 235                 240

Lys Pro Ser Ser His Asp Val Ile Thr Gly Arg Trp Ser Pro Ser Gly
                245                 250                 255

Ala Asp Gln Ala Ala Gly Arg Val Pro Gly Tyr Gly Val Ile Thr Asn
            260                 265                 270

Ile Ile Asn Gly Gly Leu Glu Cys Gly Arg Gly Gln Asp Gly Arg Val
        275                 280                 285

Ala Asp Arg Ile Gly Phe Tyr Lys Arg Tyr Cys Asp Leu Leu Gly Val
    290                 295                 300

Ser Tyr Gly Asp Asn Leu Asp Cys Tyr Asn Gln Arg Pro Phe Ala
305                 310                 315
```

<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Artificial primer.
<220> FEATURE:
<221> NAME/KEY: misc_feature
<222> LOCATION: 12, 18
<223> OTHER INFORMATION: n can be one of a,c,t, or g

<400> SEQUENCE: 4
cacgagacca cnggcggntg ggc                                           23

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Artificial primer.
<220> FEATURE:
<221> NAME/KEY: misc_feature
<222> LOCATION: 3
<223> OTHER INFORMATION: n can be one of a,c,t, or g

<400> SEQUENCE: 5
acnaatatca tcaacggcgg                                               20

<210> SEQ ID NO 6
<211> LENGTH: 771
<212> TYPE: DNA
<213> ORGANISM: Triticum aestivum
<220> FEATURE:
<221> NAME/KEY: misc_feature
<222> LOCATION: (1)..(771)
<223> OTHER INFORMATION: cDNA

<400> SEQUENCE: 6
atggcgaggt tgctgccct cgccgtgtgc gccgccgcgc tcctgctcgc cgtggcggcg      60
gggggtgccg cggcgcaggg cgtgggctcg gtcatcacgc ggtcggtgta cgcgagcact    120
ctgcccaacc gcgacaactc gctgtgcccg gccagagggt tctacacgta cgacgccttc    180
atcgccgccg ccaacacctt cccgggcttc ggcaccaccg cagcgccga cgacatcaag    240 cgcgacctcg ccgccttctt cggccagacc tcccacgaga ccaccggagg gacgagaggc    300

```
gctgccgacc agttccagtg gggctactgc ttcaaggaag agataagcaa ggccacgtcc      360
ccaccatact atggacgggg acccatccaa ttgacagggc ggtccaacta cgatcttgcc      420
gggagagcga tcgggaagga cctggtgagc aacccagacc tagtgtccac ggacgcggtg      480
gtgtccttca ggacggccat gtggttctgg atgacggcgc agggaaacaa gccgtcgtgc      540
cacaacgtcg ccctacgccg ctggacgccg acggccgccg acaccgctgc cggcagggta      600
cccggatacg gagtgatcac caatatcatc aacggcgggc tcgagtgcgg aatgggccgg      660
aacgacgcca acgtcgaccg catcggctac tacacgcgct actgcggcat gctcggcacg      720
gccaccggag gcaacctcga ctgctacacc cagaggaact cgctagcta g                771

<210> SEQ ID NO 7
<211> LENGTH: 972
<212> TYPE: DNA
<213> ORGANISM: Triticum aestivum
<220> FEATURE:
<221> NAME/KEY: misc_feature
<222> LOCATION: (1)..(972)
<223> OTHER INFORMATION: cDNA

<400> SEQUENCE: 7
atgtccacgc tgagagcgcg gtgtgcgacg gccgtcctgg ccgtcgtcct ggcggcggcc      60
gcggtcacgc cggccacggc cgagcagtgc ggctcgcaag ccgcggcgc caagtgcgcc      120 gactgcctgt gctgcagcca gttcgggttc tgcggcacca cctccgacta ctgcggcccc      180
cgctgccaga gccagtgcac tggctgcggt ggcggcggcg gcgggtggc ctccatcgtg      240 tccagggacc tcttcgagcg gttcctgctc catcgcaacg acgcagcgtg cctggcccgc      300
gggttctaca cgtacgacgc cttcttggcc gccgccggcc gttcccggc cttcggcacc      360 accggagacc tggacacgcg gaagcgggag gtggcggcct tcttcggcca gacctctcac      420
gagaccaccg gcgggtggcc caccgcgccc gacggcccct tctcatgggg ctactgcttc      480
aagcaggagc agggctcgcc gccgagctac tgcgaccaga gcgccgactg gccgtgcgca      540
cccggcaagc agtactatgg ccgcggcccc atccagctca cccacaacta caactacgga      600
ccggcgggcc gcgcaatcgg ggtggacctg ctgaacaatc cggacctggt ggccacggac      660
ccgacagtgg cgttcaagac ggcgatatgg ttctggatga cgacgcagtc caacaagccg      720
tcgtgccatg acgtgatcac ggggctgtgg actccgacgg ccagggatag cgcagccgga      780
cgggtacccg ggtatggtgt catcaccaac gtcatcaacg gcgggatcca atgcggcatg      840 ggcagaacg acaaggtggc ggatcggatc gggttctaca gcgctattg tgacattttc      900 ggcatcggct acgggaataa cctcgactgc tacaaccaat tgtcgttcaa cgttgggctc      960
gcggcacagt ga                                                         972

<210> SEQ ID NO 8
<211> LENGTH: 960
<212> TYPE: DNA
<213> ORGANISM: Triticum aestivum
<220> FEATURE:
<221> NAME/KEY: misc_feature
<222> LOCATION: (1)..(960)
<223> OTHER INFORMATION: cDNA

<400> SEQUENCE: 8
atgagaggag ttgtggtggt ggccatgctg gccgcggcct tcgccgtgtc tgcgcacgcc      60
gagcaatgcg gctcgcaggc cggcggggcg acgtgcccca ctgcctctg ctgcagcaag      120
```

-continued

```
ttcggtttct gcggcaccac ctccgactac tgcggcaccg gctgccagag ccagtgcaat    180
ggctgcagcg gcggcacccc ggtaccggta ccgacccct ccggcggcgg cgtctcctcc    240
attatctcgc agtcgctctt cgaccagatg ctgctgcacc gcaacgacgc ggcgtgcctg    300 gccaagggt tctacaacta cggcgccttc gtcgccgccg ccaactcgtt ctcgggcttc    360
gcgaccacag gtagcaccga cgtcaagaag cgcgaggtgg ccgcgttcct cgctcagact    420
tcccacgaga cgaccggcgg gtggccgacg gcgcccgacg gccctactc ctggggctac    480 tgcttcaacc aggagcgcgg cgccacctcc gactactgca cgccgagctc gcagtggcca    540
tgtgcgccgg gcaagaagta cttcgggcgc gggcccatcc agatctcaca caactacaac    600
tacgggccgg cggggcaggc catcggcacc gacctgctca acaacccgga ccttgtggcg    660
tcggacgcga ccgtgtcgtt taagacggcg ttgtggttct ggatgacgcc gcaatcaccc    720
aagccttcga gccacgacgt gatcacgggc cggtggagcc cctcgggcgc cgaccaggcg    780
gcggggaggg tgcctgggta cggtgtgatc accaacatca tcaacggtgg gctcgagtgc    840
gggcgcgggc aggacggccg tgtcgccgac cggatcgggt tctacaagcg ctactgcgac    900
ctccttggcg tcagctacgg tgacaacctg gactgctaca accaaaggcc gttcgcatag    960
```